United States Patent [19]

Zimmermann et al.

[11] 4,224,313
[45] Sep. 23, 1980

[54] PHYSIOLOGICAL PREPARATION CONTAINING LOADED CELLS IN SUSPENSION AND AN AGENT FOR COUNTERACTION OF CELL MEMBRANE DISINTEGRATION

[75] Inventors: Ulrich Zimmermann, Jülich; Günter Pilwat, Niederzier; Karin Bock, Aachen; Hermann-Josef Buers, Jülich, all of Fed. Rep. of Germany

[73] Assignee: Kernforschungsanlage Jülich Gesellschaft mit beschrankter Haftung, Jülich, Fed. Rep. of Germany

[21] Appl. No.: 859,240

[22] Filed: Dec. 9, 1977

[30] Foreign Application Priority Data

Dec. 9, 1976 [DE] Fed. Rep. of Germany ....... 2655801

[51] Int. Cl.$^2$ .................... A61K 37/48; A61K 43/00; C12B 3/12; A61K 35/14
[52] U.S. Cl. ..................................... 424/94; 128/1.1; 424/1; 424/101; 435/2
[58] Field of Search ..................... 195/1.8; 424/101, 94

[56] References Cited

U.S. PATENT DOCUMENTS 3,887,698  6/1975  McConnell et al. ................. 424/88

FOREIGN PATENT DOCUMENTS 2326224  5/1974  Fed. Rep. of Germany .
2326161 12/1974  Fed. Rep. of Germany .
2326191 12/1974  Fed. Rep. of Germany .
2405119  9/1975  Fed. Rep. of Germany .

OTHER PUBLICATIONS

U. Zimmerman et al., Biochim. et Biophys. Acta, 436 (1976), 460–474.
U. Zimmerman et al., Biochim. et Biophys. Acta, 375 (1975), 209–219.
U. Zimmermann et al., Chemical Abstracts 85:29784z, (1976), Enzyme loading of electrically homogeneous human red blood cell ghosts prepared by dielectric breakdown.
U. Zimmermann et al., Chemical Abstracts 82:108324r, (1975), Preparation of erythrocyte ghosts by dielectric breakdown of the cell membrane.
U. Zimmermann et al., Chemical Abstracts 81:75566v, (1974), Reversible dielectric breakdown of cell membranes in electrostatic fields.

*Primary Examiner*—Donald G. Daus
*Assistant Examiner*—M. C. Eakin
*Attorney, Agent, or Firm*—Flynn & Frishauf

[57] ABSTRACT

A material capable of forming hydrogen bonds or covalent bonds with loading materials incorporated in loaded cells is introduced into the cells with the loading materials to inhibit the destruction of the cell membranes by the loading material after the permeability of the membranes is brought back down to its normal value. In order to provide for the hydrogen bond formation with common loading materials, such as methotrexate, proteins such as albumin and sugars such as sucrose are effective. The time period during which these materials inhibit a destructive effect on the membranes of loaded cells is well defined. Accordingly, when cells are loaded with a medicament for interaction with substances external to the cells in a physiological solution in which they are placed, which materials have no destructive effect on the cell membranes, it is advantageous to load the cells also with a material having such a destructive effect, such as pronase P, and at the same with a sugar or a protein for delaying its effect, so that the medicament will be released by destruction of the cell membranes after a predetermined time. In this manner, by injection into an animal bloodstream of a suspension of loaded cells prepared according to the invention suspended in a physiological solution, the timing of the release of a medicament into the bloodstream can be controlled.

6 Claims, No Drawings

PHYSIOLOGICAL PREPARATION CONTAINING LOADED CELLS IN SUSPENSION AND AN AGENT FOR COUNTERACTION OF CELL MEMBRANE DISINTEGRATION

This invention relates to a process of preparation of a physiological solution containing a mass of loaded cells in suspension, such cells having a concentration of material loaded therein designed for chemical or physical interaction with substances located outside of the cell membrane. In such a process, the permeability of living animal cells of the kind having a cell membrane suspended in a cell-compatible solution is increased by the effect of osmotic pressure or by the effect of an electric field. In such a process, also, the interaction material or materials are drawn out of the surrounding cell-compatible solution by permeation through the cell membranes of which the permeability has been increased, by simultaneous exchange with the cell content in the interior of the cells to be loaded, and then the material or materials in question are locked in the cells by regeneration of the cells that heals the changes produced in the cell membrane by the effect of osmotic pressure or by the effect of an electric field, after which the loaded cells are separated from the cell-compatible solution containing the loading material and are suspended for preservation and storage in a physiological solution having an osmolarity that corresponds to the osmolarity of the content of the loaded cells. The term "osmolarity" refers to a concentration of particles of molecular size in terms of the osmotic pressure, so that the preceding statement refers to a solution in which osmosis will not occur during storage.

Processes of the above kind for preparation of a suspension of loaded cells in a physiological solution are known from German Pat. No. 23 26 244 and from German published patent applications (OS) 23 26 161 and 24 95 119. The patent just mentioned relates to processes for incorporating of complex-forming materials in loaded cells obtained from living cells of living organisms. The processes disclosed in German (OS) No. 23 26 161 concern the incorporation of catalytically active materials such as enzymes or pharmaceutics in loaded cells. Both of the processes just mentioned seek to increase the permeability of the cell membrane by the action of osmotic pressure on the membrane. In the process disclosed in German (OS) 24 05 119, on the other hand, the increase of the permeability is obtained by the effect of an electric field.

In addition to the designation "loaded cells" which is intended to express that the cells are "loaded" with materials that are distinct from the normal cell content, other terms have been used for the products of the known processes of the above-described kind, such as "membrane vesicles", "ghost cells" and "membrane envelopes".

As cells for the known processes for preparing a mass of suspended loaded cells, there are used both cells that occur as individual cells in a physiological solution, as for example erythrocytes, lymphocytes, thrombocytes or leukocytes and also cells, such as for example liver cells, that are organized in tissues as associations of cells clinging one to another. The cell binding of a tissue is releasable by biochemical or biophysical procedures, so that in this fashion also a suspension of cells in a solution can be obtained.

In the performance of the known processes, particularly for incorporation of extraneous materials in the loaded cells, a specific property of the membrane of living cells is used, namely that a permeability increase produced within certain limits can be reduced back to normal healing through regeneration of the cells. The healed membrane of the loaded cells thus regains the semipermeable properties of the membrane of the original cells. Apart from the cases in which materials are used which destroy the membrane after their incorporation in the loaded cells and are thereby set free, it is then possible to bring the material incorporated in the loaded cells into interaction with substances present in a physiolgical solution outside of the loaded cells without the material incorporated and locked in the loaded cells getting into the physiological solution. This takes place when the loaded cells are immersed into the physiological solution containing the substances in question and the substance, by permeation, gets through the semipermeable membranes of the loaded cells. It is thus, for example, possible, with the enzyme invertase locked in loaded cells, to convert cane sugar (sucrose) into glucose and fructose, since cane sugar as well as glucose and fructose get through the membrane, while the enzyme invertase remains locked in the loaded cells. It is also possible, for example, to load cells with urease and then to inject the loaded cells thus produced into the blood vessels of a human body without releasing the urease out of the loaded cells into the blood, and thereby to break down urea contained in the blood which penetrates into the loaded cells.

It has been found, however, that a great many of the materials incorporated and locked in loaded cells enter into interaction with the cell membrane and this interaction has the result of destroying the cell membrane. The loaded cells produced according to the known methods make no provision for any restraint or other influence on the progress of the destruction of the cell membrane in the manner just mentioned and for that reason, loaded cells prepared according to the known processes, in the cases in which the cell membrane is attacked, are either used only for a very limited time that can be very short according to the nature of the interaction with the cell membrane, or else such loaded cells are regarded as not useable at all.

THE PRESENT INVENTION

It is an object of the present invention to provide a process for preparing a mass of loaded cells suspended in a physiological solution of the above-described type with which it is possible to lock in the loading material in the loaded cells for a considerable time exceeding a predetermined minimum for a predetermined time.

Briefly, when the loading material, if loaded alone in the loaded cells, would lead to premature destruction of the cell membrane, additional material for loading in the interior of the cells having raised cell membrane permeability is provided in the solution of said loading material, which additional materials form hydrogen bonds or covalent bonds with the loading material that is provided for interaction with substances that may be present outside the loaded cells. The result is that the loading materials are unable to react with the membrane, while their intended effect is nevertheless not impaired. The dosing in the physiological solution provided for material exchange is such that after the incorporation of the main loading material and the additional material in the loaded cells, the interaction of the materials with the cell membrane is hindered for a predetermined time.

In application of the process of the invention, to give an example, the material methotrexate, that is used for treating tumors but nevertheless attacks the cell membrane, is incorporated in loaded cells together with a protein, for example albumin, or with a sugar, for example sucrose or a similar polysaccharide, with the result that the membranes of the loaded cells remain stable about twice as long as would be the case without the addition of protein or sugar. By use of the process according to the invention, therefore, the range of application of the known processes are extended in a highly advantageous manner.

In the case of loading materials that are compatible with the cell membrane and therefore cause no destruction of the cell membrane, by another aspect of the invention dealing with the same problem of providing the preservability of loaded cells for a predetermined period, there is loaded, through the cell membranes when they have increased permeability, along with the aforesaid loading material, a material that does have a destructive effect on the cell membrane which is introduced in the physiological solution provided for the material exchange in such dosing that, after the healing of the cell membrane and the separation of the loaded cells from the solution containing the loading materials, the cell membranes of the loaded cells will be destroyed after a predetermined time.

If for example a mass of membrane vesicles is produced with erythrocytes as a starting cell material, in accordance with the invention, in which the enzyme arginase that is used in enzyme deficiency diseases, together with a predetermined dose of a material having a destructive effect on the cell membranes, as for example proteolytic enzymes and substances producing the breakdown of lipids (pronase, phospholiphase, trypsin), then after injecting the cells so loaded into the blood circulation system of an animal body, the medicament is set free in the body after a predetermined time and thus brought into action. It is of course possible to inject into a blood vessel a mixture of loaded cells with different doses of the cell membrane destroying agent and in that way to control in a predetermined manner the progress of the liberation of the medicament in the body.

The applicability of a mass of loaded cells prepared by the process of the present invention extends thus far beyond the field of application of the loaded cells prepared according to the heretofore known processes. The loaded cells produced by the processes according to the invention can, according to their particular purpose, be introduced either as semipermeable holders for materials designed for interaction with substances present outside the cell membrane or, on the other hand, as carriers for materials that will be set free from their contained condition after a predetermined time. A fully new field is thus opened up, particularly for medical application.

It has been found particularly useful to introduce a cell-membrane destroying agent into the cell-compatible solution provided for material exchange through the membrane in such dosing, that after the healing of the cell membranes and the separation of the loaded cells, the cell membranes of the loaded cells are destroyed after a predetermined time, taking account of the addition to the loading materials of materials that inhibit the destruction of the cell membranes by formation of hydrogen bonds (sometimes referred to as "hydrogen bridges") or by formation of covalent bonds, and not relying on the loading materials designed to interact with substances in the solution outside the cell membranes for the membrane-destructive effect. In that way it is possible to reduce to a negligible contribution the undesired effect of a loading material provided merely for the interaction with substances that may be present outside the cell membranes, for example the agent 6-fluoro-uracil sometimes used for chemotherapy against cancer, and to provide the intended destruction of the cell membranes solely by the effect of the agent provided particularly for that purpose, whereby a better time control of the desired destruction of the cell membranes is brought about.

In the performance of the process according to the invention, the permeability increase of the cell membranes can be produced either by the effect of osmotic pressure or by the effect of an electric field, as may be desired according to the requirements of the particular case.

For the case that the teaching provided in the above-cited German patent and German OS No. 23 26 191 regarding permeability increase by the operation of osmotic pressure, the process of the present invention can be carried out as follows:

The cells provided for the preparation of the mass of loaded cells are first put into a cell-compatible solution that, for example, can be an aqueous solution containing at least 0.5 mM per liter of magnesium and/or calcium ions as well as potassium ions, the solution having an osmolarity that is so low compared with the osmolarity of the cell content that, as the result of the osmotic pressure thereby produced in the cells, the permeability of the cell membranes is increased—without however destroying the membranes.

Erythrocytes are used for preparation of the loaded cells. The osmolarity difference to be provided amounts approximately to a factor of 15. If the cell-compatible solution does not already contain the materials to be loaded into the cells, this material should then at this point be added. Furthermore, the materials to be included in the cells in accordance with the present invention are also introduced into the cell-compatible solution in the appropriate dosing. After the material exchange between the materials present in the cell-compatible solution and the cell contents through the cell membranes now having an increased permeability, and the content of the thus produced loaded cells practically corresponds to that of the cell-compatible solution, as a next step, the osmolarity of the cell-compatible solution is increased to that of the original cell content by the addition of the osmotically active materials, such as calcium, potassium and sodium ions. By osmotically active materials there are here understood materials that have a reflection coefficient of about 0.8, but, however, because they are in general contained in a cell-compatible solution, build up a sufficiently high osmotic pressure. After a dwell time, during which the cell membranes heal up, the loaded cells so formed are separated from the cell-compatible solution and the mass of loaded cells thus produced is poured into an isotonic physiological liquid. When erythrocytes are used, it is practical, for healing away the changes of the cell membranes produced by permeability increase, to let the cells stand for about five minutes at 0° C. and then to warm them up to body temperature for about 30 to 60 minutes.

For the case in which the teaching of German OS No. 24 05 119 regarding permeability increase by the effect of an electric field is to be used, the performance of the method of the present invention is carried out as follows:

The cells provided for the preparation of the mass of loaded cells are put into an electrically conducting liquid forming a cell-compatible electrolyte solution which is preferably at a temperature lying between 0° C. and 25° C. As a next step, the electrolyte solution containing the cells is subjected to an electric field having a strength from $10^3$ to $10^5$ V/cm until the permeability of the cell membranes is increased to such an extent that molecules with a radius of at least 0.5 nm can pass through the cell membranes. For this purpose, it is convenient and practical to pass the electrolyte solution through a focus of an electric field. The resulting permeability increase can be recognized, for example in the application of the process to erythrocytes, by the discoloration of the electrolyte liquid as the result of the hemoglobin going out of the cell interiors and by the decoloration of the erythrocytes. In the case in which the materials and substances that are to be incorporated in the loaded cells are already in the cell-compatible electrolyte solution, the material exchange takes place right after the permeability increase. It is however also possible, after the permeability increase and still before the performance of the healing of the cell membranes, to put the cells into a cell-compatible solution of which the osmolarity corresponds to the osmolarity of the cell content of the original cells. In this cell-compatible solution, in which are contained the materials to be loaded into the cells, the material exchange between these materials and the cell content then takes place. After a dwell time in which the cell membranes heal, the loaded cells thus formed are separated from the cell-compatible solution and the mass of loaded cells thus prepared is then poured into an isotonic physiological solution for preservation and storage. When erythrocytes are used, it is practical to prepare the loaded cells in a potassium chloride solution and then to transfer the loaded cells into an isotonic sodium chloride solution that corresponds to blood serum in its ion concentration and osmolarity.

EXAMPLE I

Erythrocytes, obtained from citrated blood by new stages of centrifuging are suspended in a solution in the ratio of one part by volume of erythrocytes to ten parts by volume of the solution, the solution containing:

105 mM KCl; 20 mM NaCl; 4 mM $MgCl_2$; 7,6 mM $Na_2HPO_4$; 2.4 mM $NaH_2PO_4$ and 10 mM glucose.

The pH value of the solution was 7.2

10 ml of the suspension so produced was exposed to an electrical field strength of 12 kV/cm at 0° C. in an apparatus suitable for the purpose for 40usec. About one minute after the application of the electrical field that was followed with hemolysis, 5 mM per liter of methotrexate that had been marked with tritium and 0.1% by volume of albumin was added to the solution. After the hemolysis, that lasted about five minutes, the solution was held for another five minutes at 0° C. in order that an equilibrium could be reached between the cell interiors and the external solution that contained the methotrexate. As a next step, the temperature of the solution was raised to 37° C., in order to accelerate the healing-up of the changes produced by the electric field in the membranes. The healing-up process was terminated after about twenty minutes. The loaded cells were then centrifuged out for ten minutes under an accelerative force 10,000 times the value of the acceleration of gravity, and the sediment of loaded cells thus obtained was suspended in a physiological solution that has the following composition:

138.6 mM NaCl; 12.3 mM $Na_2HPO_4$; 2.7 mM $NaH_2PO_4$.

The pH value of the solution was 7.4 and the suspension concentration of the solution 6%. In order to determine the effect of the locked-in albumin, after twenty hours, the loaded cells were centrifuged out of the solution and the radioactivity in the solution and in the still intact loaded cells was measured. The same measurements were carried out on loaded cells that were prepared in the same manner as described above, but without inclusion of albumin. A comparison of the measured values showed that after twenty hours 33% more intact cells with locked-in albumin were present than there were without locked-in albumin.

EXAMPLE II

The loaded cells were produced in the manner described in Example I, but instead of the addition of methotrexate and albumin into the solution containing the erythrocytes, sucrose that had been marked with the radio-nuclide C 14 and also pronase P were added to the solution containing the erythrocytes, still before the application of the electric field. The sucrose content in the solution was 10 mM and that of pronase P was 0.01 mg per 100 ml.

The effect of the pronase P locked in the loaded cells was, as described in Example I, determined by measurement of the radioactivity in the loaded cells and by comparison with loaded cells in which sucrose, but no pronase P had been locked in. After twenty hours, the quantity of intact cells containing pronase P was only 11% of the quantity of intact loaded cells in which no pronase P had been locked in.

EXAMPLE III

The loaded cells were produced as described in Example I, except that instead of the addition of methotrexate and albumin to the solution containing erythrocytes, methotrexate that had been marked with tritium, albumin and phospholiphase C were added to the solution, still before the application of the electric field. The content of methotrexate was 5 mM, the content of albumin 0.1% by volume and the content of phospholiphase C 0.01 mg per 100 ml.

As shown by a comparative measurement for a case in which no phospholiphase C had been incorporated, after twenty hours only 17% of the intact loaded cells were present compared to the number of them found in the comparison measurement.

EXAMPLE IV

For preparation of loaded cells by the effect of osmotic pressure, erythrocytes were suspended in a volume ratio of 1:1 in an isotonic, phosphate-buffered NaCl solution of the following composition:

138.6 mM NaCl; 12.3 mM $Na_2HPO_4$; 2.7 mM $NaH_2PO_4$.

The pH value of the solution was 7.4.

1 ml of the suspension so produced was added, for increasing the permeability of the membranes of the cells, with stirring, to 10 ml of a solution that contained 5 mM of methotrexate that had been marked with tritium, 4 mM of MgSo$_4$ and 50 mM of sucrose. This solution was allowed to stand five minutes at 0° C. As the next step, the osmolarity of the original solution was restored by adding a corresponding quantity of a 2 molar KCl solution. The solution was then allowed to stand another five minutes at 0° C. and immediately thereafter the temperature was raised for twenty minutes to 37° C. in order to accelerate the healing of the membranes. The loaded cells so produced were centrifuged out of the solution, after which the cells were incubated in an isotonic, phosphate-buffered sodium chloride solution of the above-given composition. The loaded cells so produced contained practically the same concentration of methotrexate as the external medium, namely 98%.

A comparative measurement for checking the holding capability of the loaded cells produced showed the same results as in Example I.

Although the process of the present invention has been illustrated with reference to particular examples, it will be understood that variations and modifications are possible within the inventive concept.

Just as the suspensions of loaded cells in physiological solutions prepared according to previously known methods, the suspension of loaded cells in physiological solutions prepared according to the present invention are usable both for the treatment of animals and for the treatment of human beings. In the case of treatment of human beings, it is of course desirable to use human cells for the starting material in the preparation of the loaded cell suspension: erythrocytes from human blood, for example. The present invention widens the applicability for medical and other physiological treatment of loaded cell suspension which, as prepared according to previously known methods, have already established a certain acceptability for use in medical and physiological treatment. It should be mentioned that the additives introduced in the cell-loading step in accordance with the present invention for inhibiting the destruction of cell membranes by other loading materials by the formation of hydrogen bonds or covalent bonds are classes of materials, represented by proteins and sugars, regarding which there is a great deal of information available regarding the compatibility of such materials with the blood of human patients.

The terms "animal cells" and "animal body" as used herein, therefore, are to be understood as including human cells and a human body, respectively.

We claim:

1. A process for preparing a mass of loaded cells suspended in a solution, which cells by their loading are provided with material intended for chemical or physical interaction with substances present outside the cells, comprising the steps of suspending living animal cells selected from the group consisting of erythrocytes, lymphocytes, thrombocytes and leucocytes, and having cell membranes, in a cell-compatible solution, increasing the permeability of the cell membranes by the effect of osmotic pressure, or by the effect of an electric field, or both, incorporating loading material selected from the group consisting of medicaments and radionuclides into the cells by passage of said material from a cell-compatible solution through the membranes of increased permeability, restoring the original permeability of the membranes by healing up the membranes by regeneration effect, then separating the cells from the solution in which they were suspended and putting them for preservation in suspension in a physiological solution of the same osmolarity as the loaded cell content, said process incorporating the improvement consisting in that:

in the step of incorporating loading material into the cells, a medicament material having a capability of reacting chemically or physically with substances in physiological solution outside the cell, is incorporated which is of a kind which when so incorporated without the incorporation of any other material would prematurely destroy the cell membranes, and at least one additional material selected from the group consisting of blood-compatible sugars and proteins which are capable of providing hydrogen-bridge-bonding with said medicament material or of entering into covalent bonds therewith is incorporated along with said medicament material into said cells to such an extent that the reaction of said medicament material with the cell membranes is inhibited while its intended capability for interaction with substances external to the loaded cells is not thereby impaired, said additional material being added to said cell-compatible solution used in said incorporating step in such dosing that after incorporation of said medicament and said additional material in the loaded cells the interaction of said first material with the cell membrane is inhibited for a predetermined time.

2. A process for preparing a mass of loaded cells suspended in a solution, which cells by their loading are provided with material intended for chemical or physical interaction with substances present outside the cells, comprising the steps of suspending in a cell-compatible solution living animal cells selected from the group consisting of erythrocytes, lymphocytes, thrombocytes and leucocytes, and having cell membranes, increasing the permeability of the cell membranes by the effect of osmotic pressure, or by the effect of an electric field, or both, incorporating loading a medicament material into the cells by passage of said medicament material from a cell-compatible solution through the membranes of increased permeability, restoring the original permeability of the membranes by healing up the membranes by regeneration effect, then separating the cells from the solution in which they were suspended and putting them for preservation in suspension in a physiological solution of the same osmolarity as the loaded cell content, said process incorporating the improvement consisting in that:

in the step of incorporating material into the cells, a first material is incorporated which is of a kind which is compatible with the cell membranes and therefore produces no destruction of the cell membranes, which first material is selected from the group consisting of medicaments having a capability of reacting chemically or physically with substances in physiological solution outside the cell, and there is also incorporated into the loaded cells, at the time their cell membranes have an increased permeability, a second material added to the cell-compatible solution utilized in said step of incorporating material, said second material being selected from the group consisting of enzymes capable of decomposing proteins and enzymes capable of decomposing lipids, and having a gradual destructive effect on the cell membranes and being supplied with such dosing in said cell-compatible solution, that after the healing up of the cell membranes and the separation of the loaded cells from the solution containing materials to be incorporated in the cells, the cell membranes will be destroyed after a predetermined period of time.

3. A process as defined in claim 1, in which in the step of incorporating loading material into the cells, a second additional material is provided in the cell-compatible solution used in said step and is thereby incorporated in the loaded cells, which second additional material is a material selected from the group consisting of enzymes capable of decomposing proteins and enzymes capable of decomposing lipids, and having a gradual destructive effect on the cell membrane, said additional material being provided in said physiological cell-compatible solution in such dosing, that after the healing up of the cell membrane and the separation of the loaded cells from the solution used in the material-incorporating step, the cell membranes of the loaded cells will be destroyed in a predetermined period of time.

4. A mass of loaded cells suspended in a physiological solution containing a first material extraneous to the original cell content which is a medicament capable of chemical or physical interaction with substances contained in physiological solution external to the cells and which has a destructive effect on the membrane of the cells, and containing also a second material selected from the group consisting of blood-compatible sugars and proteins which are capable of forming hydrogen bonds or covalent bonds with said first material and thereby inhibiting said destructive effect on the cell membranes for at least a predetermined period of time.

5. A mass of loaded cells suspended in a physiological solution in which the cells contain a first material selected from the group consisting of medicaments having a capability of reacting chemically or physically with substances in physiological solution external to the cells and also a second material selected from the group consisting of enzymes capable of decomposing proteins and enzymes capable of decomposing lipids, and having a gradual destructive effect on the cell membranes, said second material being present in such relative quantity that the cell membranes are not destroyed thereby until a predetermined time after the preparation of the said suspension of loaded cells in said physiological solution.

6. A mass of loaded cells suspended in a physiological solution as defined in claim 5, in which said loaded cells contain a third material selected from the group consisting of blood-compatible sugars and proteins which are capable of forming hydrogen-bridge-bonds or covalent bonds with said second material and thereby inhibiting the destructive effect of said second material on the membranes of the cells for a predetermined period of time.

* * * * *